United States Patent [19]
Doty et al.

[11] Patent Number: 5,374,825
[45] Date of Patent: Dec. 20, 1994

[54] DIGITAL TANNING MONITOR

[76] Inventors: J. Stephen Doty, 1817 James St., Jonesboro, Ark. 72401; Richard Baxter, Jr., 2 Meadowbrook La., Appleton, Wis. 54914; Robert W. Colburn, 2964 Sonoran Trail, Green Bay, Wis. 54313

[21] Appl. No.: 976,181

[22] Filed: Nov. 13, 1992

[51] Int. Cl.$^5$ .......................... G01J 1/42; G01J 1/00
[52] U.S. Cl. ................................ 250/372; 250/494.1
[58] Field of Search ................ 250/492.1, 494.1, 372; 606/11

[56] References Cited
U.S. PATENT DOCUMENTS 4,279,254  7/1981  Boschetti et al. ............ 250/372 EM
5,107,123  4/1992  Shi ............................... 250/372 EM Primary Examiner—Bruce C. Anderson
Attorney, Agent, or Firm—Crutsinger & Booth

[57] ABSTRACT

An apparatus and method are provided for measuring and controlling the amount of UV light exposure for tanning purposes. The UV light is measured using a photo diode to produce an analog signal with a strength corresponding to the intensity of the UV light emitted. A microprocessor converts the signal to a digital quantity and integrates the digital quantity over time to determine the accumulated amount of UV light emitted. The quantity of instantaneous or accumulated UV light emitted can be displayed. The accumulated UV light exposure can also be used to control the operation of the UV light bulbs.

24 Claims, 10 Drawing Sheets

DIGITAL TANNING MONITOR

TECHNICAL FIELD

The present invention relates to the measurement and control of ultraviolet light intensity and exposure for tanning purposes.

BACKGROUND OF THE INVENTION

The traditional method of measuring and controlling a tanning ultraviolet (UV) light source is through the use of a timer. The timer is preset for a fixed amount of time and the UV light source is activated for the duration of the prescribed time interval.

This method has several shortcomings, for example, it does not account for variations in UV light intensity, such as created by variations in UV bulbs that arise from alternating current (AC) power line fluctuations, bulb wear, and lot-to-lot variations of bulbs and ballast circuits. Thus, for a given tanning session, the user may be subjected to more or less tanning radiation than is desired. It is possible that a tanning session based only upon time may exceed the FDA-prescribed maximum exposure defined as four times the minimal erythema dose (MED) for untanned Type II skin.

SUMMARY OF THE INVENTION

This invention contemplates new apparatuses and methods that monitor a UV light source by measuring the actual UV light intensity.

A photo diode measures the instantaneous intensity of UV light output from a tanning bulb or bank of bulbs. The photo diode generates an analog current with a strength corresponding to the intensity of the UV light. An amplifier converts the current to a voltage signal and amplifies it to a proper level for a microprocessor. The microprocessor then converts the analog signal to a digital value representing the instantaneous UV light intensity. A display module displays information such as the intensity of UV light, time, etc.

In a variation of the apparatus, the microprocessor integrates the measured intensity of UV light over time to yield the accumulated exposure. A display module displays the accumulated amount of UV light.

In a further variation of the apparatus, a memory module stores the desired amount of UV exposure. The apparatus periodically compares the accumulated UV exposure with the desired amount of UV exposure. When the accumulated UV exposure equals or exceeds the desired UV exposure, the microprocessor sends a signal to activate an alert or to activate a relay to remove power from the UV bulbs to automatically terminate the tanning session.

It can be advantageous to use in the apparatus, an optical filter that discriminates against non-UV light. The photo diode then receives the UV light passing through the filter to more accurately measure the UV light exposure in the tanning apparatus.

A method used herein to monitor UV light exposure comprises the following steps: exposing a photo diode to the UV light to be measured to generate a current that has a strength in proportion to the intensity of the UV light, converting the current to a voltage, amplifying the voltage, converting the voltage from an analog value to a digital quantity, and displaying the digital quantity. A variation of the invention further comprises integrating the digital quantity of UV light intensity over time and displaying the accumulated quantity.

Another variation of the invention additionally comprises entering a predetermined quantity of UV light exposure into a memory unit, periodically testing to determine whether the accumulated quantity equals or exceeds the predetermined quantity, and activating a relay to remove power from the UV light source if the accumulated quantity equals or exceeds the predetermined quantity.

The objects of this invention are to provide apparatuses and methods that do one or more of the following: (1) accurately measure actual UV light exposure, (2) integrate the UV light exposure over time to determine an accumulated UV light exposure, and (3) control the operation of UV lights by removing power from them when the accumulated UV light exposure equals or exceeds a predetermined amount of exposure. The invention overcomes the inherent limitations of prior art systems that only approximate exposure based on the time that UV bulbs operate.

BRIEF DESCRIPTION OF THE DRAWINGS

The accompanying drawings are incorporated into and form a part of the specification to illustrate an example of the present invention. These drawings, together with the description, serve to explain the principles of the invention. The drawings are only for illustrating preferred and alternative examples of how the invention can be made and used and are not to be construed as limiting the invention to only the illustrated and described examples. The various advantages and features of the present invention will be apparent from a consideration of the drawings in which.

Numeral references are employed to designate like parts throughout the various figures of the drawing.

DETAILED DESCRIPTION OF THE PREFERRED EMBODIMENTS

Figure 1:
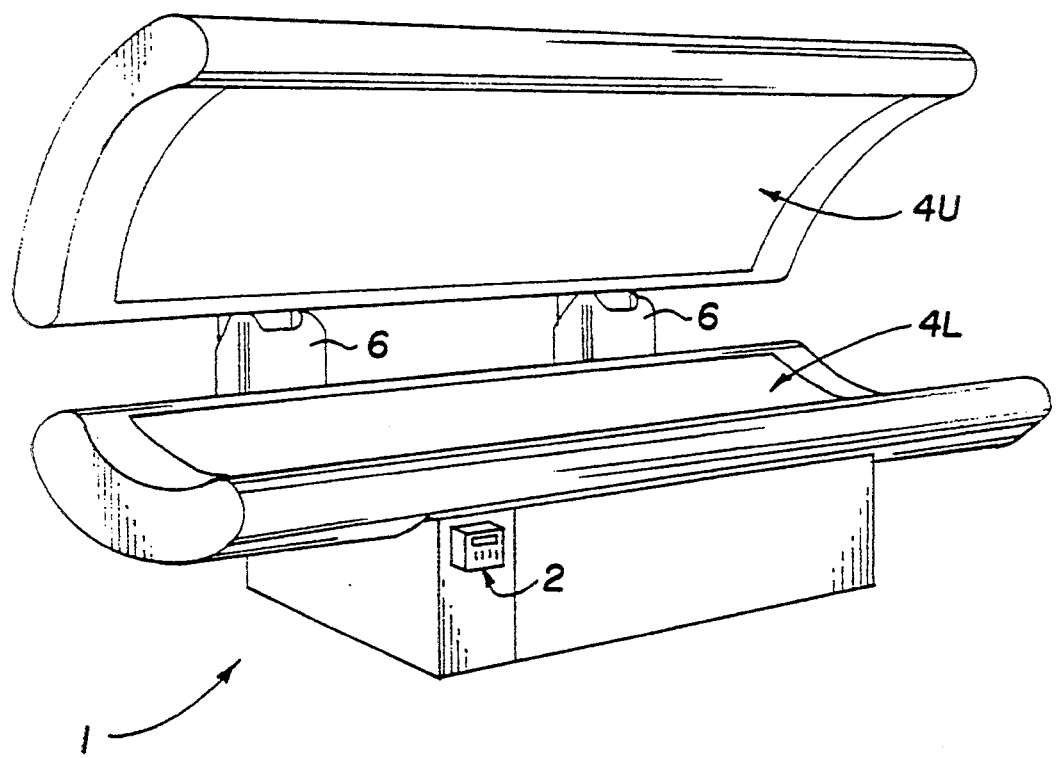
FIG. 1 is an illustration of a sun tan bed unit with a digital monitor.

The present invention will be described by referring to the drawings showing various examples of how the invention can be made and used. In these drawings, reference characters are used throughout the several views to indicate like or corresponding parts.

FIG. 1 illustrates typical sun tanning bed 1 with monitor 2 according to the present invention attached to it. Monitor 2 requires little space. Sun tanning bed 1 includes a lower and an upper bank of UV bulbs 4L and 4U, respectively. The upper bank of UV bulbs 4U is pivotally supported at hinges 6. The photo diode is not shown due to its small size; however, the photo diode is placed where it can accurately measure the UV light intensity from bulb banks 6L and 6U.

Figure 2:
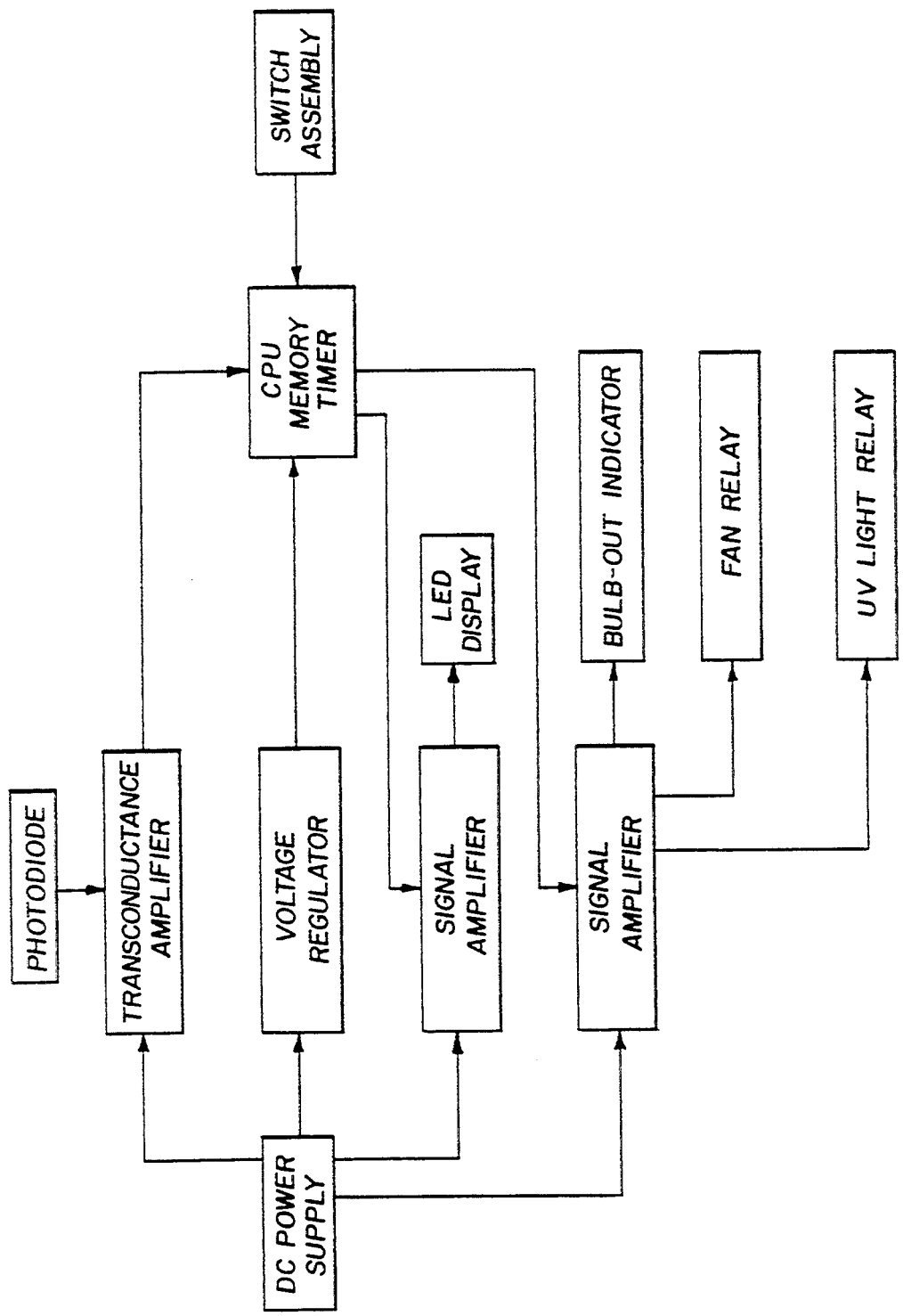
FIG. 2 is a block diagram showing the logical relationship of different functions of the monitor.

FIG. 2 is a block diagram showing the major components of the monitor. A power supply provides direct current (DC) to the other components of the monitor. A voltage regulator is used to accurately control the DC power supplied to the microprocessor (CPU), memory, and timer. The photo diode generates an analog current proportional to the intensity of UV light. The transconductance amplifier converts the current into an analog voltage and amplifies it for the microprocessor. The switch assembly controls the microprocessor, memory, and timer. The microprocessor converts the analog voltage signal from the amplifier to a digital quantity. The microprocessor uses the timer to integrate the digital quantity over time to determine the accumulated amount of UV exposure. When the accumulated amount of UV exposure reaches a specified quantity, a signal is sent through a signal amplifier to the UV light relay to turn the UV bulbs off. After the UV bulbs are turned off, a signal can be sent through a signal amplifier to the fan relay to keep the fan on for a period of time. The microprocessor also controls the display so that the instantaneous or accumulated UV light intensity or other information can be displayed by sending a control signal through a signal amplifier to a numeric display comprising light emitting diodes (LEDs).

Figure 3A:
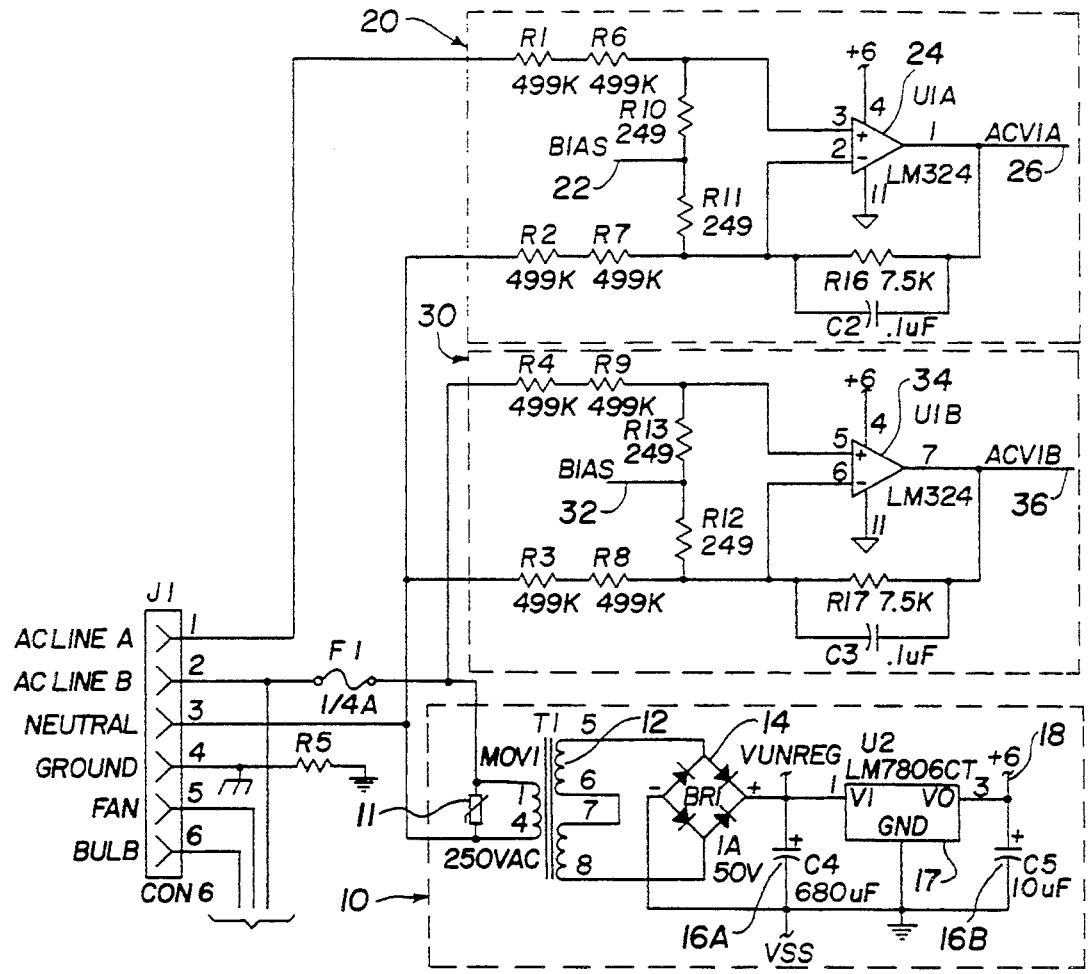
FIG. 3A is a circuit diagram of the monitor power assembly.

FIG. 3A illustrates, in greater detail, power supply 10 and voltage meters 20 and 30 for the monitor. Power supply 10 employs a design that is well-known to those skilled in the art and converts 120 volts of alternating current (AC) into 6 volts of direct current (DC) through output 18 for the monitor. It comprises metal oxide varister 11, transformer 12, bridge rectifier 14, filter capacitors 16A and 16B, and voltage regulator 17. Metal oxide varister 11 prevents damage to the monitor from reasonable AC line transient conditions. Voltage regulator 17 is commercially available from National Semiconductor Corporation as Part No. LM7806CT.

Voltage meters 20 and 30 measure the value of the voltage supplied to power supply 10 in a manner well known to those skilled in the art. The supplied voltage, 240 volts from a single-phase, four-wire source, comprises 120 volts on one wire, 120 volts on the other wire, a neutral wire, and a ground wire. Voltage meter 20 measures one side of the voltage, biased at lead 22, through operational amplifier 24; voltage meter 30 measures the other side of the voltage, biased at lead 32, through operational amplifier 34. Signal 26 represents the analog value of the voltage being measured by voltage meter 20 and is input to AN7 pin 35 of central processing unit (hereinafter "CPU") 100. Signal 36 represents the analog value of the voltage being measured by voltage meter 30 and is input to AN6 pin 34 of CPU 100.

Figure 3B:
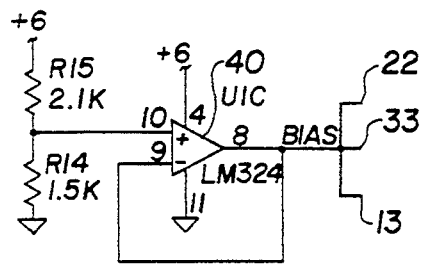
FIG. 3B is a circuit diagram of the bias generator.

Referring to FIG. 3B, bias generator 40 employs a technique well known to those skilled in the art to measure analog signals using a single power supply instead of a positive and a negative power supply. It establishes a 2.5 volt DC reference and buffers it for lead 22 of volt meter 20, lead 32 of volt meter 30, and pin 33 of CPU 100. CPU 100 subtracts the bias signal from signals 26 and 36 that it receives from voltmeters 20 and 30 to get an absolute value of voltage from the power sources. Bias generator 40, as well as operational amplifiers 24 and 34, are on a single chip available from Motorola as Part No. LM324N.

Figure 4:
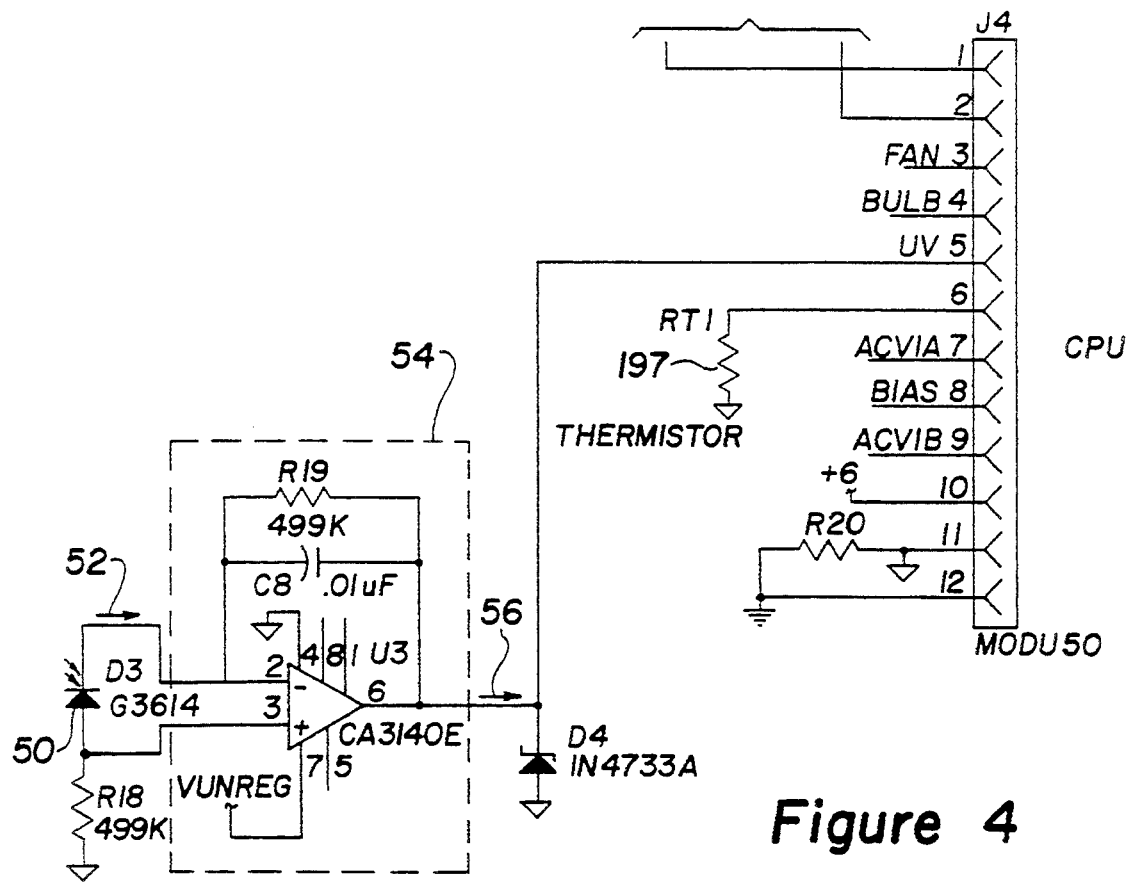
FIG. 4 is a circuit diagram of the photo diode and transconductance amplifier.

Referring to FIG. 4, photo diode 50 receives light that passes through a UV light filter, which can be physically integral with photo diode 50 or a separate part. The UV light passed through the filter can include both UV-A and UV-B light. In response to the UV light, photo diode 50 generates in line 52 a current with a strength corresponding to the intensity of the UV light that the photo diode is exposed to. Transconductance amplifier 54 converts the current in line 52 to the analog voltage at line 56 which is then amplified to a proper value for CPU 100. The analog voltage at line 56 is fed through CPU pin 32 into CPU 1.00 which then converts the analog signal to a digital format suitable for further processing. Photo diode 50 with the integral UV filter is commercially available from Hamamatsu as Part No. G3614.

Figure 5A:
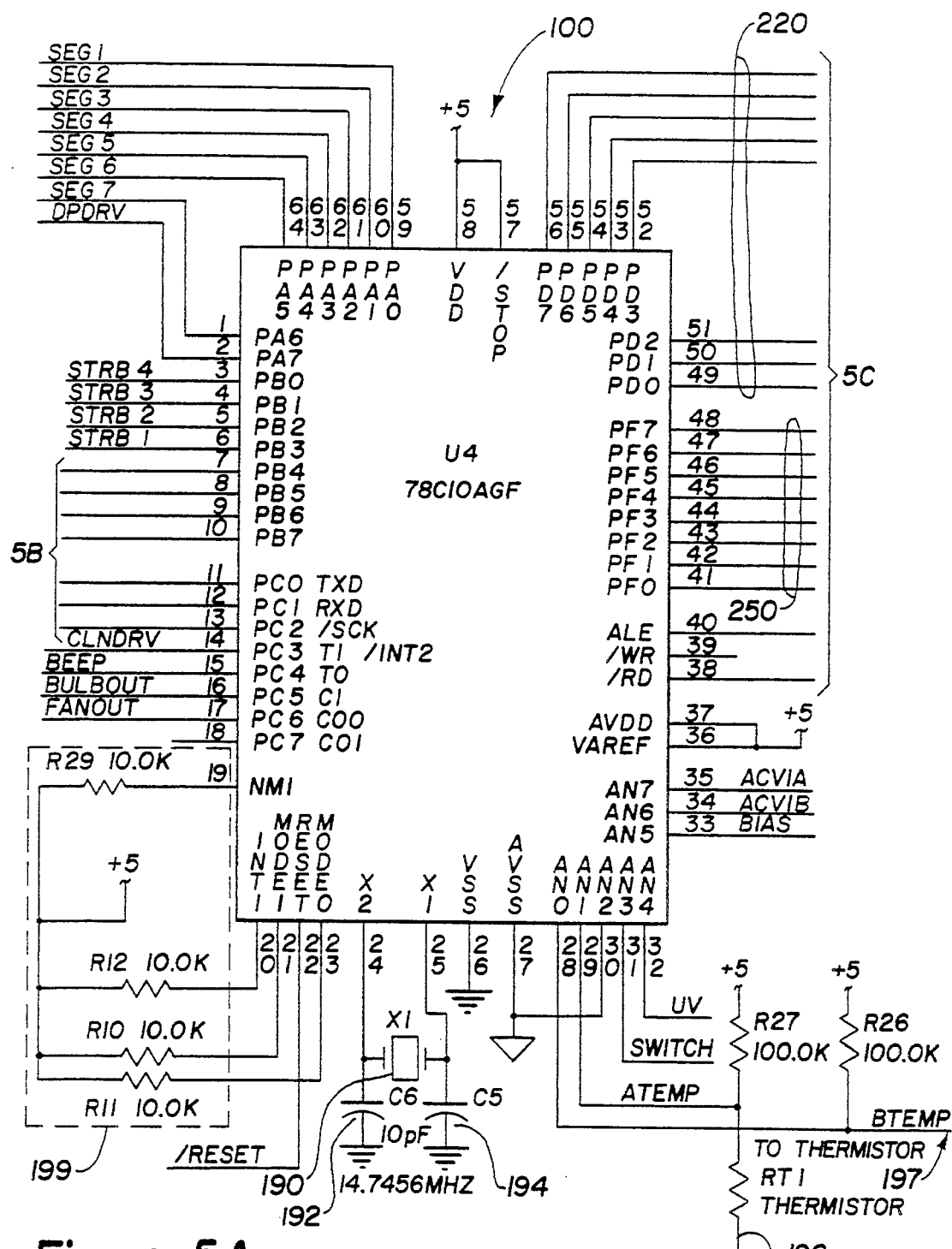
FIG. 5A-C are a circuit diagram illustrating how the central processing unit and memory unit are connected to the monitor.
Figure 5B:
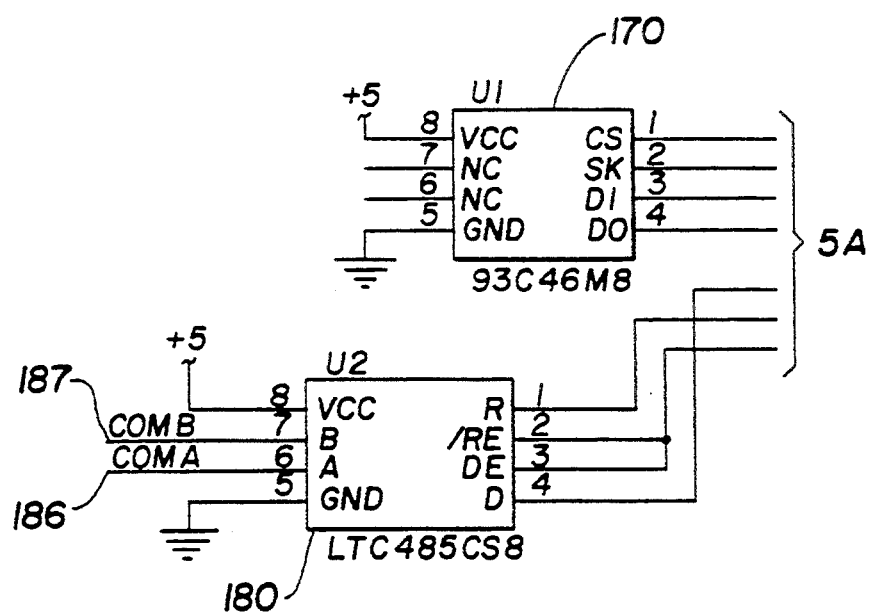

Referring to FIG. 5A, CPU 100 is the microprocessor for the monitor. The microprocessor is physically integral with the monitor unit and includes a clock and a plurality of analog-to-digital signal converters. It is commercially available from NEC Electronics, Inc. as Part No. UPD78C10AGF.

Figures 6, 7:
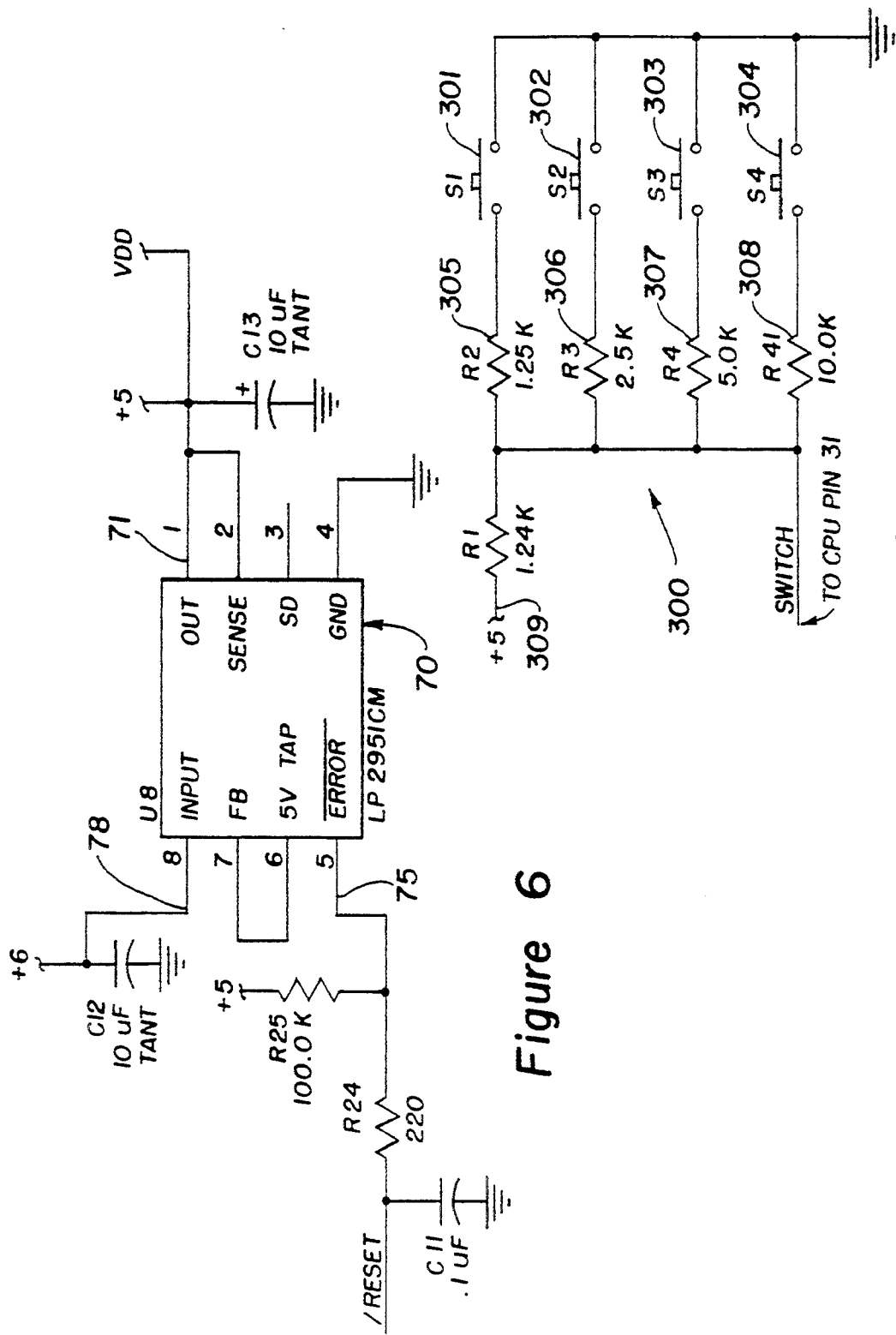
FIG. 6 is a circuit diagram of the voltage regulator chip and associated pins.
FIG. 7 is a circuit diagram of the switched resister circuit.

CPU 100 is powered by voltage regulator chip 70 as shown in FIG. 6. Chip 70 receives 6 volts from power supply output lead 18 into input pin 8 of chip 70. Chip 70 delivers 5 volts on output pin 1 of chip 70 to VAREF pin 36 and VDD pin 58 of CPU 100. Chip 70 also provides an error output signal through pin 5 of chip 70 to RESET pin 22 of CPU 100. Whenever power to CPU 100 is in any way disrupted, the error output signal acts as a "power on" reset to direct CPU 100 to restart the processing of instructions beginning at the start of the program stored in memory unit 200. Chip 70 is commercially available from National Semiconductor Corporation as Part No. LP2951CM.

Figure 5C:
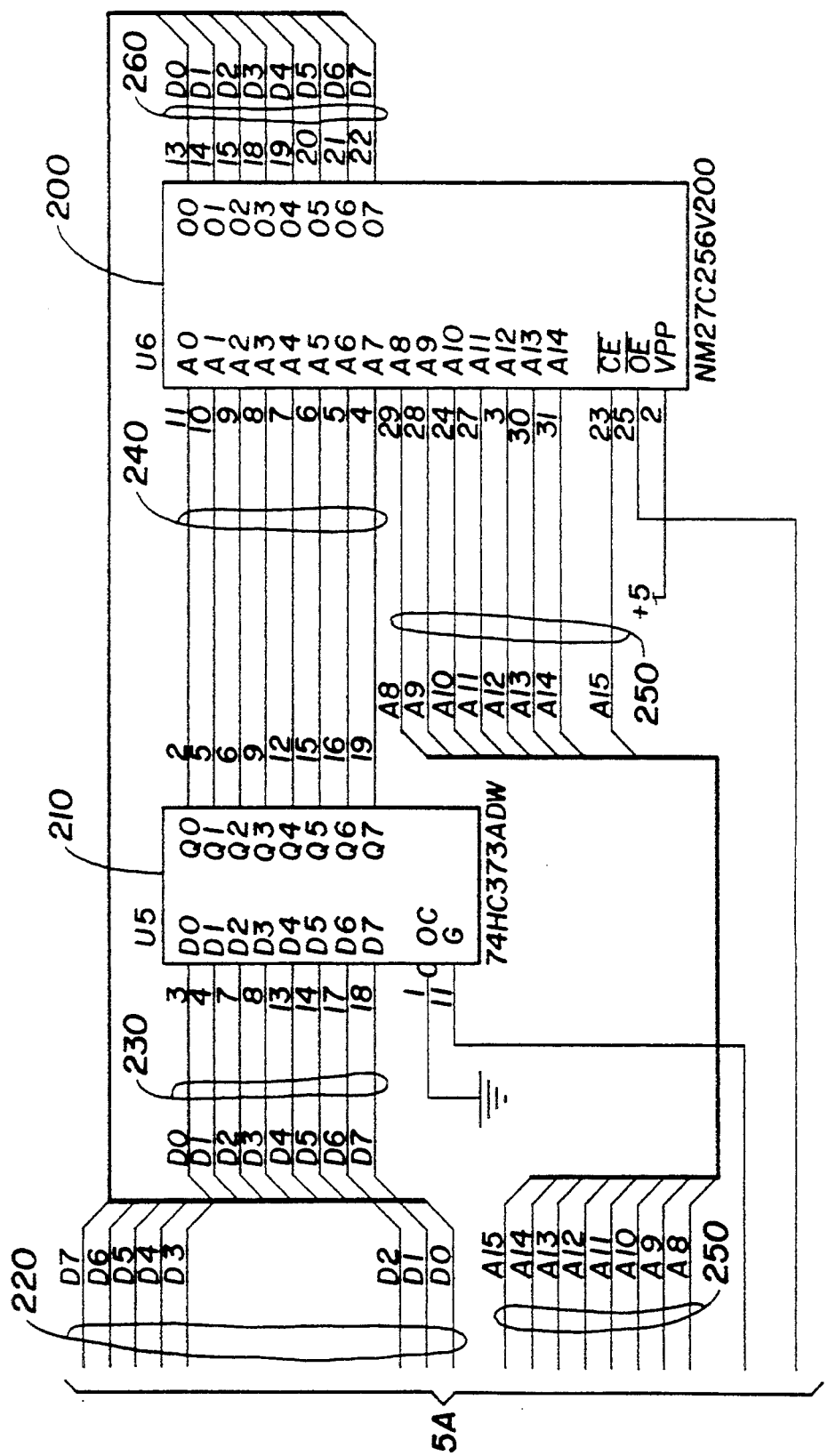

Referring to FIG. 5C, external memory unit 200 stores the software or firmware that drives CPU 100. Memory unit 200, commercially available from National Semiconductor Corporation as Part No. NM27C256-V200, is an OTP (One-Time Programmable) memory chip and has capacity for 32 kilobytes of program data. Memory chip 200 is connected to CPU 100 through latch chip 210 which is commercially available from Motorola as Part No. 74HC373ADW.

Latch chip 210 is used to buffer communications between components such as CPU 100 and memory chip 200 because, in the preferred embodiment, the CPU does not contain sufficient pins to fully address external memory 200. For CPU 100 to interact with external memory 200 as shown in FIGS. 5A and 5C, 16 address lines and 8 data lines are required. However, CPU 100 has only 8 address lines and 8 data lines. To compensate for this shortage from CPU 100 of 8 address lines, CPU 100 transmits the first 8 bits of address information through CPU pins 49-56 and data bus 220 for a short period of time (less than a millisecond). This information is then transferred through bus 230 to latch chip 210 where it resides until CPU 100 toggles a signal, called the "Address Latch Enable" signal, through CPU ALE pin 40. When latch chip 210 receives the Address Latch Enable signal, it latches the 8 bits of address information it received out through address bus 240 while CPU 100 simultaneously transmits 8 bits of address information through CPU pins 41–48 and address bus 250 to memory chip 200. Memory chip 200 thus receives 16 bits of address information. Upon receipt of the address information, memory chip 200 retrieves the data stored at the indicated memory address and transmits it through data buses 260 and 220 into CPU pins 49–56.

Memory unit 170 is used to store operating parameters that can change periodically. Memory 170 is a serial, non-volatile, EEPROM (Electrically Erasable Programmable Read-Only Memory) memory chip used for storing information such as fan-delay time, session-delay time, network address, reference digital calibration factors, total accumulated time that UV bulbs have been operating, and other information that can change periodically, but which should not be lost when power is removed from the chip. The calibration factors can be used to reduce system errors and accurately measure line voltage metering signals, temperature metering signals, and UV light intensity metering signals. Memory chip 170 has sufficient capacity to store 1,024 bits of data (64 words using 16 bits per word) and is commercially available from National Semiconductor Corporation as Part No. 93C46M8.

Communications interface chip 180 is used to buffer low current signals from CPU TXD transmitter pin 11 and CPU RXD receiver pin 12 so they can drive a twisted pair of wires on the output side of chip 180 from COM-A pin 6 and COM-B pin 7 of chip 180. COM-A and COM-B form a bi-directional differential network implementing the well-known industry standard RS-485 communications protocol which enables the CPUs of up to 31 monitors (as, for example, in a tanning salon) to communicate with a remote computer or a hand-held remote control. Chip 180 is commercially available from Linear Technology Corporation as Part No. LTC485C98.

Crystal 190 and 10 pF capacitors 192 and 194 provide a 14.7456 MHz oscillator for CPU 100 at CPU X1 pin 25 and CPU X2 pin 24.

Thermister 196 monitors the ambient temperature of the circuit board that CPU 100 resides on and converts the temperature to an analog voltage that is input to AN1 pin 29 of CPU 100. Thermister 197 monitors the temperature of the tanning bed and converts that temperature to an analog voltage that is input to AN0 pin 28 of CPU 100. These two analog signals are converted to digital signals by CPU 100. Each thermistor is commercially available from Midwest Components, Inc. as Part No. 1H104.

CPU 100 implements a non-maskable interrupt signal from CPU NMI pin 19 and another interrupt signal from CPU INT1 pin 20. Two other CPU signals are transmitted from CPU MODE1 pin 21 and CPU MODE0 pin 23 respectively. These four signals serve no purpose for the monitor and are connected, or "tied off," to power supply 10 through resister network 199, comprising four 10,000 ohm resisters.

Referring to FIG. 7, multiple key activation sequence switch assembly 300 comprises four switches 301, 302, 303, and 304 which are coupled in series with parallel resisters 305, 306, 307, and 308, respectively, to form a resister ladder. Resister 305 provides 1,250 ohms of resistance, resister 306 provides 2,500 ohms of resistance, resister 307 provides 5,000 ohms of resistance, and resister 308 provides 10,000 ohms of resistance. Thus, each resister 306, 307, and 308 provide twice the resistance of respective resisters 305, 306, and 307. Five volts are input into switch assembly 300 at lead 309. Each resister operates to decrease the output voltage in an amount proportional to its resistance if and only if its corresponding switch is closed. Thus, for example, if switch 301 is closed, resister 305 will operate to decrease the input voltage accordingly. Each of the four switches may be open or closed in any combination. Because there are four switches that can each be either open or closed, there are 2 to the power of 4, or 16, different combinations of ways that the four switches could be set. Furthermore, because each switch is coupled with one resister, and the resistance of each resister differs from another resister by a factor of 2 to the power of $\pm 1$, 2, or 3, there are 16 discrete analog voltages that can be output depending on how the switches are set. This analog voltage output is sent to CPU AN3 pin 31 which converts it to a 4-bit digital value, in which each of the 4 bits correspond to one of the 4 switches.

A resister ladder such as switch assembly 300 conserves CPU pins. To input 16 discrete voltage levels, or 4 bits, into CPU 100 would normally require 4 pins; switch assembly 300 allows for a 4-bit input using only one pin.

In the preferred embodiment, switches 301–304 are push button switches. When switch 301 is depressed, CPU 100 interprets the resulting signal as a toggle signal to start or stop the monitor. When switch 302 or 303 is depressed, CPU 100 interprets the resulting signal as one to increase or decrease respectively the time of the tanning session. Similarly, when switch 304 is depressed, CPU 100 interprets the resulting signal as one to reset the monitor time to zero.

Switch assembly 300 could also be used in conjunction with non-volatile memory unit 170 as a security measure to prevent unauthorized users from viewing, adjusting, or resetting its parameters by first requiring the switches to be singly open or closed in a certain order.

The CPU transmits signals through CPU pins 1–6, 14, and 59–64 that ultimately drive display assembly 350. The signals may indicate instantaneous or accumulated MEDs of UV exposure, remaining time of UV exposure (in the form Minutes/Seconds), instantaneous or average CPU or bed temperature, instantaneous or average voltage supplied, or, if the decimal point on the first LED module is flashing, that the network is accessing the individual timer unit. Display assembly 350 comprises four, red, 0.3 inch, LED (light emitting diode), digital display modules 360, 370, 380, and 390. Each display module comprises nine segments, seven of which may be used in combination to form any one of ten digits, and two others of which may be used to form a decimal point or a colon. The display modules are commercially available from Hewlett-Packard as Part No. HDSP-7303.

Each of the four digits are formed using a time division multiplex sequence well-known to persons skilled in the art. That is, CPU 100 transmits 9 bits to turn on or off each of the nine segments of one digit, for example, in display module 360. Then CPU 100 suspends transmitting the 9 bits to display module 360, and transmits 9 bits to turn on or off each of the nine segments of display module 370. Similarly, CPU 100 tells display module 380 and finally display module 390 which segments to turn on or off. Following display module 390, CPU 100 repeats the cycle beginning again with display module 360. It repeats this cycle every few milliseconds, updating the display modules as necessary. The following paragraphs describe this process in greater detail.

Figure 8:
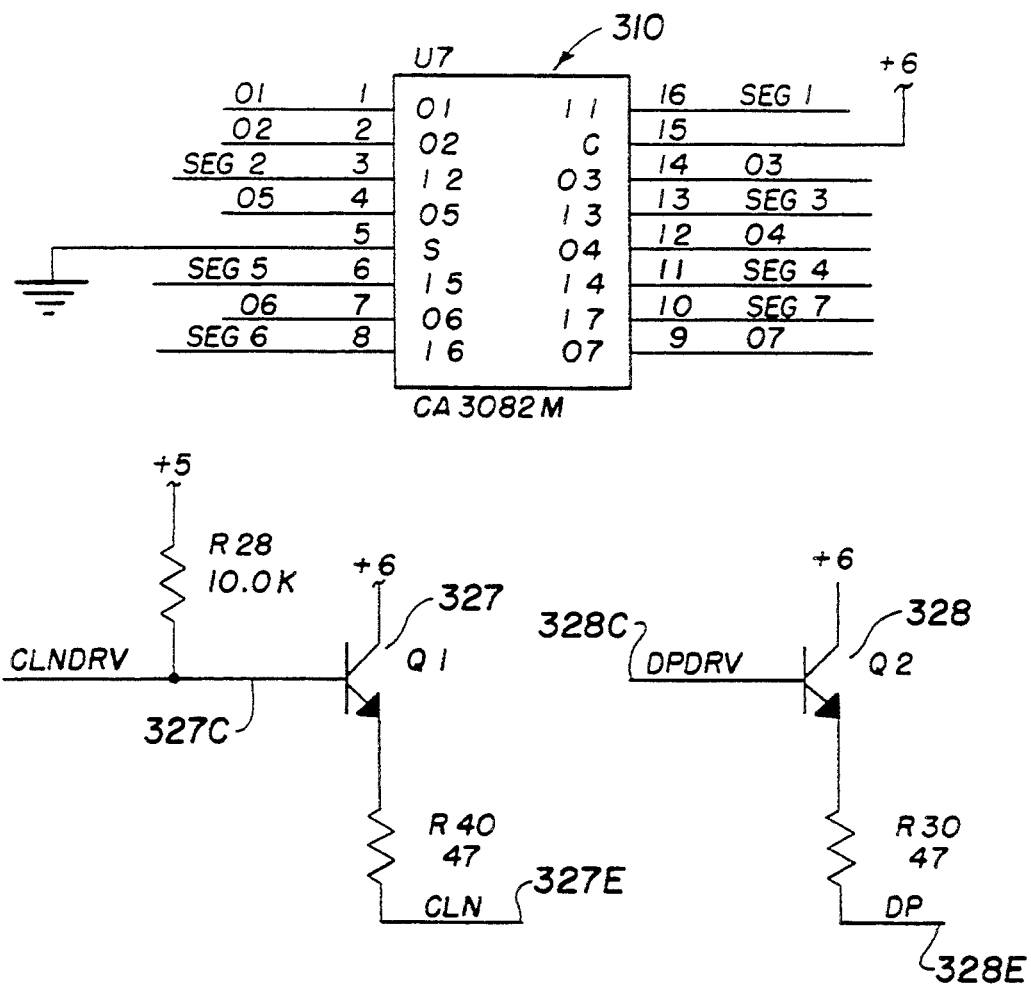
FIG. 8 is a circuit diagram illustrating how signals from the central processing unit are amplified to drive the light emitting diode display assembly.

The 9 bits of display data indicating to a particular display module (360, 370, 380, or 390) which segments to turn on or off are sent out CPU pins 59-64, 1, 2, and 14 to drive respectively segments 1-7, the decimal point, and the colon. The 9 bits are received by the display drive current amplifier assembly shown in FIG. 8, comprising chip 310 (Harris Part No. CA3082M, which further comprises an array of 7 NPN transistors), and two individual NPN transistors 327 and 328 (Motorola parts MMBT4401LT1). The 9 bits are received by pins 16, 3, 13, 11, 6, 8, and 10 of chip 310, and leads 327C and 328C respectively. The amplifier assembly amplifies the current received from CPU 100 to a level sufficient to drive LED display assembly 350. The amplified current is output through pins 1, 2, 14, 12, 4, 7, and 9 of chip 310, and leads 327E and 328E respectively.

Figure 9:
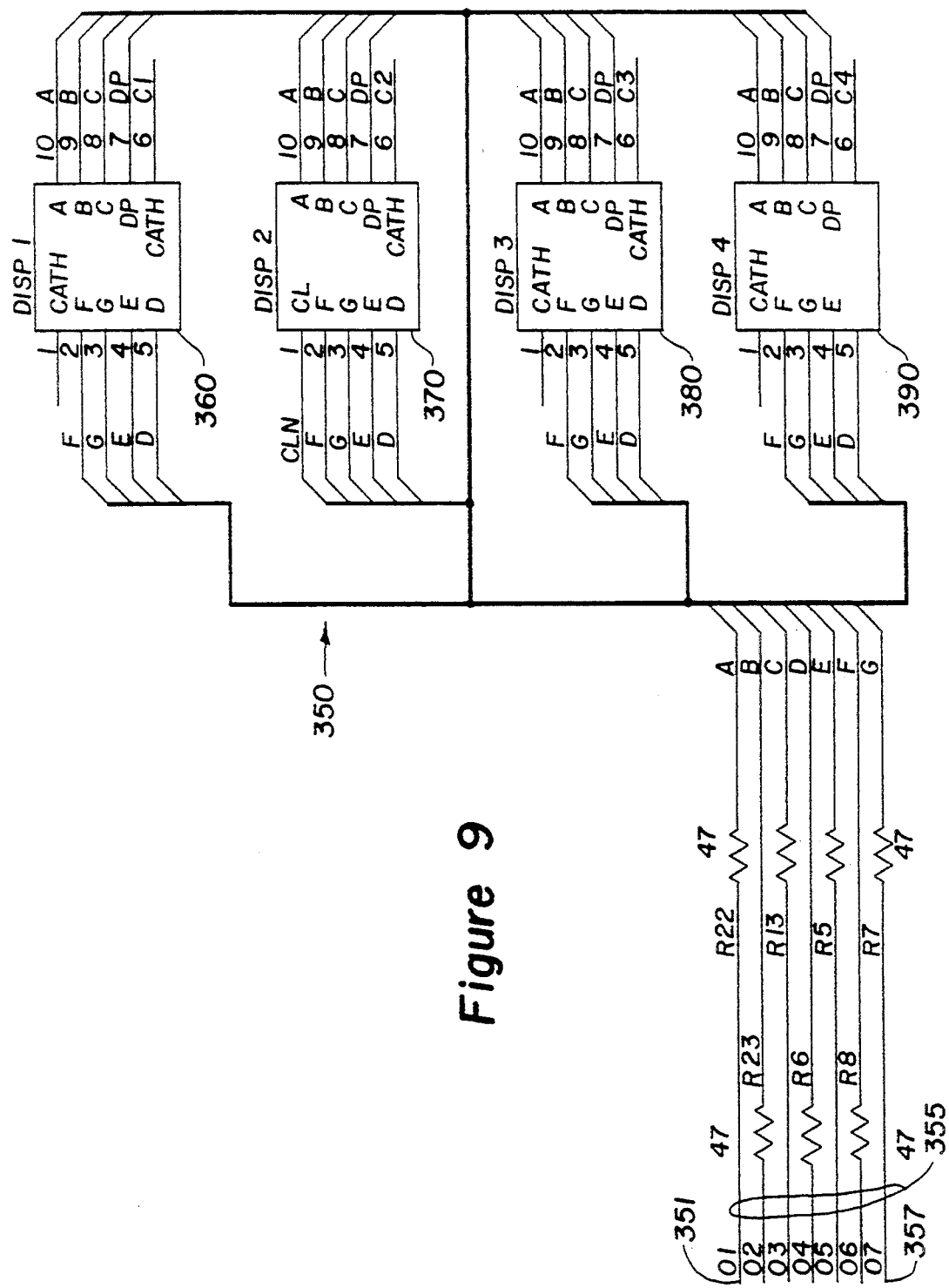
FIG. 9 is a circuit diagram of the light emitting diode display assembly.

Bits 1-7 of the 9 bits of display data are sent to leads 1-7 respectively of display assembly 350, as illustrated in FIG. 9. Bits 1-7 are then sent to pins 10, 9, 8, 5, 4, 3, and 2 respectively of display modules 360, 370, 380, and 390. The eighth bit of display data (to turn on the colon, from emitter pin 327E) is input to pin 371 of display module 370. The ninth bit of display data (to turn on the decimal point, from emitter pin 328E) is input to pins 7 of display modules 360, 370, 380, and 390. Display modules 360, 370, 380, and 390 are commercially available from Hewlett-Packard as Part No. HDSP-7303.

The 9 bits of display data are thus sent to each of the four display modules simultaneously. The multiplex function controls which display module is activated to receive and display the data represented by the 9 bits by grounding and thus permitting current flow through the display module to be activated. If display module 360 is to be activated, then CPU 100 would transmit a signal through CPU strobe pin 6. Similarly, if display module 370, 380, or 390 is to be activated, then CPU 100 would transmit a signal through CPU strobe pin 5, 4, or 3 respectively. The signal transmitted out CPU strobe pin 6, 5, 4, or 3 is then received by pin 1, 2, 3, or 4 respectively of transistor array chip 330, shown in FIG. 10, and commercially available from National Semiconductor Corporation as Part No. DS2003CM. That signal is then boosted (amplified) and transmitted to pin 6 of display module 360, 370, 380, or 390 respectively to activate the corresponding digital display module. The single digital display module that the 9 bits of signaling information are intended for is thus lit up as desired. Each of the four display modules is activated in sequence in a similar manner. The entire cycle is repeated every few milliseconds so that the human eye does not detect any flicker in the display.

The embodiment of the invention thus far described receives, from photo diode 50 and transconductance amplifier 54, an analog voltage signal proportional to the instantaneous intensity level of UV light. This signal is fed into CPU 100 which is controlled by software or firmware residing in memory unit 200. CPU 100 converts the analog voltage into a digital quantity of MEDs which is also numerically integrated over time to yield a running total of UV exposure accumulated to a given point in time during a tanning session. The quantity of MEDs can be shown on display 350 as either an instantaneous value or as an accumulated value.

The CPU also compares the instantaneous intensity of UV light to a threshold minimum intensity level which should be attained if all UV bulbs are functioning properly.

Similar to how the analog signals representing UV light intensity are managed, CPU 100 can convert the analog tanning bed and CPU ambient temperature signals fed into CPU pins 28 and 29 respectively to digital signals, between 0 and 255 degrees F., and display the value of either of the signals on display 350. The signals can also be averaged over the time of a tanning session and displayed as the average temperature, between 0 and 255 degrees F., of the tanning bed or CPU.

Likewise, CPU 100 can convert analog signals 26 and 36 representing the actual measured instantaneous value of each of the two 120 volt phases of the 240 volt power supply, fed into CPU pins 35 and 34 respectively, to digital signals, and display the values of the signals, between 0 and 200 volts, on display 350. The digital signals can also be averaged over the time of a session and displayed as the average voltages of either of the two phases of the voltage source. The instantaneous and average voltage readings can be used for diagnosing problems related to improper wiring in buildings or tanning salons, wherein the line voltages are unacceptably low for the proper functioning of the UV bulbs.

Reference calibration factors can be stored in memory unit 170 to reduce system error and permit accurate measurement of the UV light intensity metering signals, temperature metering signals, and line voltage metering signals described above.

The monitor can also store in memory unit 170 the cost, between 0.01 and 2.55 dollars, of electricity per kilowatt-hour. CPU 100 can then use this figure to calculate the actual cost, between 0 and 2.55 dollars, of the unit's previous tanning session operation. This result can be shown on display 350.

CPU 100 can cause an audible beep of various frequencies to be made. It does this by synthesizing a frequency and transmitting it as a pulse signal out CPU pin 15. The signal is received by transistor array chip 330 through pin 7 of chip 330, amplified, and sent out pin 10 of chip 330 to activate piezoelectric buzzer 348 which oscillates, producing a "beep" sound at the synthesized frequency. This can be used by the CPU, for example, to alert the user when a desired number of MEDs have been attained, or to provide audible feedback when a push-button switch is depressed. Piezoelectric buzzer 348 is commercially available from Projects Unlimited as Part No. AT-17.

The monitor stores two values in memory unit 170 that are not clearable. First, it maintains a session counter, that is, a running total of the number of times, up to 9,999 times, that the monitor has been turned on and off since the first day of operation. Second, it maintains an hour counter, that is, a running total of the number of hours, up to 9,999 hours, that have accumulated on the monitor since the first day of operation.

Figure 11:
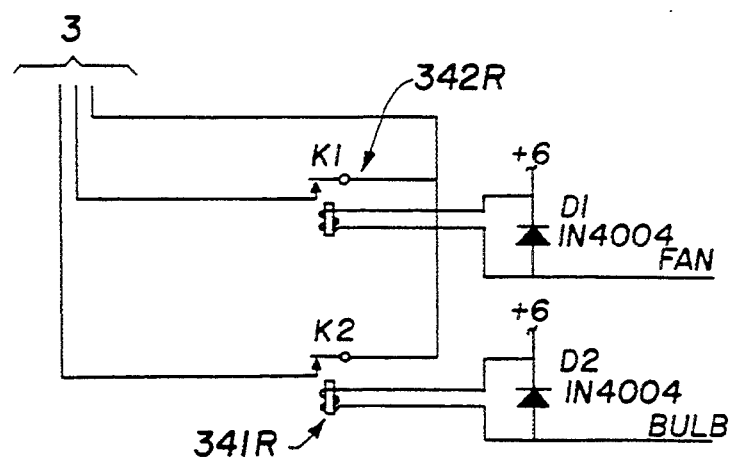
FIG. 11 is a circuit diagram of the relays that control the fan indicator.
Figure 10:
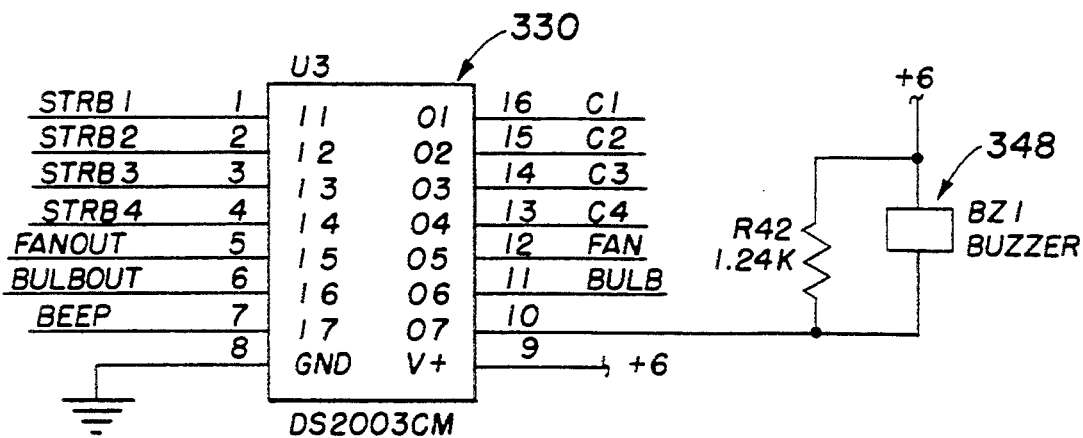
FIG. 10 is a circuit diagram of the microprocessor chip that drives the display, fan, and beeper.

The monitor provides for a post-session cooling system whereby the tanning bed cooling fan operates during the downtime between tanning sessions. CPU 100 activates the cooling fan by transmitting a signal out of CPU pin 17 into pin 5 of transistor array chip 330 (FIG. 10). Chip 330 amplifies the signal and transmits it out pin 12 of chip 330 to activate relay 342R (FIG. 11). When relay 342R is activated, it closes a switch which permits current to flow to a fan that can cool the tanning bed down. The fan can remain on for one to three minutes following a tanning session in accordance with a time value entered into memory unit 170.

CPU 100 can provide a timed countdown to operation of the tanning bed. The amount of time, between one and five minutes, can be entered in memory unit 170. When the entered amount of time has elapsed, CPU 100 can transmit a signal out CPU pin 16 to supply power to the UV lights. The signal is received by transistor array chip 330 through pin 6 of chip 330, amplified and sent out pin 11 of chip 330 to activate relay 341R (FIG. 11), which closes a switch allowing current to flow to the UV bulbs.

As part of a network, CPU 100 can identify itself as a unit between 0 and 31, in accordance with a unit number stored in memory 170, for interfacing with a front-desk console and individual units.

CPU 100 can monitor the life of a the UV bulbs by accurately logging hours, in memory unit 170, that accumulate on a lamp bank. This stored value can be cleared (i.e., when new bulbs are installed) and hours are accumulated from that point on.

In an alternate embodiment of the invention, in addition to what has been described thus far, the monitor can also control the operation of the UV bulbs. This embodiment permits a user to enter the amount of UV exposure that the user desires to receive, in units of MEDs, into memory unit 170. This desired quantity is then continuously compared with the running total of MEDs as they accumulate during that user's tanning session. When the accumulated MEDs equal or surpass the desired exposure, CPU 100 transmits a signal to alert the user or disengage a relay that would remove power from the UV light source, thus automatically terminating the tanning session.

The embodiments shown and described above are only exemplary. It is not claimed that all of the details, parts, elements, or steps described and shown were invented herein. Even though numerous characteristics and advantages of the present invention have been set forth in the foregoing description, together with details of the structure and function of the invention, the disclosure is illustrative only, and changes may be made in the detail, especially in matters of shape, size and arrangement of the parts within the principles of the invention to the full extent indicated by the broad general meaning of the terms used in the attached claims.

The restrictive description and drawings of the specific examples above do not point out what an infringement of this patent would be, but are intended to provide at least one explanation of how to make and use the invention. The limits of the invention and the bounds of the patent protection are measured by and defined in the following claims.

What is claimed is:

1. Apparatus for monitoring the proper functioning of a tanning UV light source, the UV light source being powered by an electrical line, the apparatus comprising:
   (a) means to generate an analog voltage signal in proportion to the instantaneous UV light intensity;
   (b) means to convert the analog voltage signal proportional to instantaneous UV light intensity to a digital quantity representing the instantaneous UV light intensity;
   (c) means to generate an analog signal in proportion to instantaneous line voltage of said electrical line;
   (d) means to convert the analog signal proportional to instantaneous line voltage to a digital quantity representing the instantaneous line voltage;
   (e) timer means;
   (f) means to integrate the digital quantity representing the instantaneous UV light intensity over time to determine a digital quantity representing accumulated UV light exposure; and
   (g) means to display the digital quantities representing the instantaneous UV light intensity, accumulated UV light exposure, and instantaneous line voltage of the electrical line source.

2. Apparatus as recited in claim 1, further comprising:
   (a) memory means to store a digital quantity representing a predetermined amount of UV light exposure; and
   (b) means to generate a signal when the digital quantity representing the accumulated UV light exposure equals or exceeds the digital quantity representing the predetermined amount of UV light exposure.

3. Apparatus as recited in claim 1, wherein said means to generate an analog voltage signal in proportion to the instantaneous UV light intensity comprises:
   (a) optical filter means that discriminates against non-UV light;
   (b) photo diode means to generate an analog current in proportion to the instantaneous UV light intensity that passes through said optical filter means; and
   (c) transconductance amplifier means to convert the analog current from said photo diode means to an analog voltage signal and to amplify the analog voltage signal.

4. Apparatus as recited in claim 3, wherein said means to convert the analog voltage signal to a digital quantity, said means to integrate the digital quantity representing the instantaneous UV light intensity over time, and said means to generate a signal when the digital quantity representing the accumulated UV light exposure equals or exceeds the digital quantity representing the predetermined UV light exposure comprises: microprocessor means and memory means operatively connected to said photo diode and said timer means.

5. Apparatus as recited in claim 4, wherein said means to display the digital quantities representing the instantaneous UV light intensity and accumulated UV light exposure comprises:
   (a) means to amplify the signals from said microprocessor means representing the digital quantities of instantaneous UV light intensity and accumulated UV light exposure to a proper level to control said display means; and
   (b) firmware means to direct the transmission of signals from said microprocessor means such that said display means are repeatedly activated in time division multiplex order so that said display means appear to be continuously activated.

6. Apparatus as recited in claim 5, wherein said firmware means comprises: a One-Time Programmable Memory means to store programming instructions that control said microprocessor means.

7. Apparatus as recited in claim 1, further comprising:
   (a) memory means to store a digital quantity representing a minimum threshold UV light intensity; and
   (b) means to generate a signal when the digital quantity representing the instantaneous UV light intensity is less than the digital quantity representing the minimum threshold UV light intensity.

8. Apparatus as recited in claim 1 wherein the digital quantities representing the instantaneous UV light intensity and the accumulated UV light exposure correspond to standard units of minimal erythema dose.

9. Apparatus as recited in claim 8 wherein said means to display the digital quantities representing the instantaneous the UV light intensity and the accumulated UV light exposure displays the digital quantities in analog format.

10. A monitor for a tanning apparatus, the tanning apparatus having a UV light source that receives power from an electrical line, the monitor comprising:
   (a) at least one photo diode that generates an analog current in proportion to the UV light intensity of the UV light source;
   (b) amplifier that converts the analog current to an analog voltage and that amplifies the analog voltage;
   (c) voltage meter operably connected to the electrical line that generates an analog voltage in proportion to the line voltage;
   (d) at least one display; and
   (e) microprocessor to convert the analog voltages from said amplifier and said voltage meter to digital quantities and to activate said display, whereby the instantaneous UV light intensity and the instantaneous line voltage in said electrical line can be displayed to assist in monitoring the proper functioning of the tanning apparatus.

11. A monitor according to claim 10, further comprising: data memory connected to said microprocessor to store programming codes and other data for use by said microprocessor.

12. A monitor according to claim 11, further comprising: a clock that provides elapsed time data to said microprocessor so that said microprocessor can determine the accumulated UV light exposure by integrating the digital quantity representing the UV light intensity over the elapsed time provided by said clock and control said display whereby the accumulated UV light exposure can be displayed.

13. A monitor according to claim 12, further comprising: a relay connected to said microprocessor that can disengage power from the UV light source of the tanning apparatus, whereby when the accumulated UV light exposure equals or exceeds a predetermined amount of UV light exposure stored in said data memory, said microprocessor activates said relay to disengage power from the UV light source to automatically terminate tanning.

14. A monitor according to claim 13, further comprising: a switch assembly having:
   (a) switch to increase the predetermined amount of UV light exposure; and
   (b) switch to decrease the predetermined amount of UV light exposure.

15. A monitor according to claim 11, further comprising: security means requiring the entry of a code before the stored data in said data memory can be altered.

16. A monitor according to claim 15, wherein said security means comprises:
   (a) a plurality of resisters connected in parallel, wherein the resistance of any two resisters differs by a factor of two to an integral power;
   (b) a plurality of switches, one switch connected in series to each individual resister such that the number of said switches is equal to the number of said resisters;
   (c) a voltage supply to send a voltage through said plurality of resisters and switches such that the total voltage drop across said plurality of resisters is discrete and depends on which switches are open or closed; and
   (d) microprocessor to convert the discrete voltage from an analog to a digital signal, the digital signal comprising bits equal in number to the number of said switches; each bit being equal to zero if a switch is open and equal to one if a switch is closed; access being granted to alter the contents of the monitor's memory only if a certain combination of switches are closed to enter a correct password number.

17. A monitor according to claim 11, wherein the tanning apparatus has a cooling fan and wherein the monitor further comprises: relay connected to said microprocessor to control power to the cooling fan whereby said microprocessor activates said relay to activate said cooling fan for a specified period stored in said data memory and measured by said clock after said tanning apparatus UV lights are turned off.

18. A monitor according to claim 10, further comprising:
   (a) thermistor connected to said microprocessor to provide ambient temperature data to said microprocessor; and
   (b) thermistor connected to said microprocessor to provide tanning apparatus temperature data to said microprocessor,
   whereby said microprocessor can activate said display to display the ambient temperature data and tanning apparatus temperature data.

19. A monitor according to claim 10, further comprising:
   (a) direct current power supply; and
   (b) voltage regulator that controls the power delivered to said microprocessor by said direct current power supply.

20. A method for monitoring UV light exposure from a tanning unit and monitoring the proper functioning of the tanning unit, comprising the steps of:
   (a) generating an analog voltage signal in proportion to the instantaneous intensity of UV light emitted from said tanning unit UV light source;
   (b) converting the analog voltage proportional to the instantaneous UV light intensity to digital data representing the instantaneous UV light intensity;
   (c) generating an analog signal in proportion to the instantaneous voltage of the electrical line;
   (d) converting the analog signal proportional to the instantaneous line voltage to digital data representing the line voltage;
   (e) integrating over time the digital data representing the instantaneous UV light intensity to determine the accumulated UV light exposure;
   (f) averaging over time the digital data representing the instantaneous line voltage;
   (g) displaying the quantity of accumulated UV light exposure; and
   (h) displaying the average line voltage.

21. The method as recited in claim 20, further comprising the steps of:
   (a) storing a predetermined quantity of UV light exposure;
   (b) testing whether the accumulated UV light exposure equals or exceeds the predetermined UV light exposure; and
   (c) sending a signal to a relay when the accumulated UV light exposure equals or exceeds the predetermined UV light exposure, such that upon receipt of the signal, power is disengaged from the UV light source of the tanning unit.

22. The method as recited in claim 20, wherein generating an analog voltage in proportion to the instantaneous UV light intensity comprises the steps of:
   (a) filtering out non-UV light;
   (b) exposing a photo diode to the filtered UV light so that an analog current is generated in proportion to the instantaneous intensity of the UV light that the photo diode is exposed to;
   (c) converting the current from the photo diode to a voltage signal; and
   (d) amplifying the voltage signal.

23. The method as recited in claim 20, further comprising the steps of:
   (a) storing a value representing a minimum threshold UV light intensity level;
   (b) testing whether the UV light intensity is less than the minimum threshold intensity; and
   (c) signaling when the UV light intensity is less than the minimum threshold intensity.

24. The method as recited in claim 20, further comprising the steps of:
   (a) monitoring the ambient temperature;
   (b) monitoring the tanning unit temperature; and
   (c) displaying the ambient temperature and the tanning unit temperature.

* * * * *